United States Patent [19]

Morelle et al.

[11] 4,447,366

[45] May 8, 1984

[54] DERIVATIVES OF LYSINE AND ASPARTIC ACID

[76] Inventors: Jean V. Morelle; Eliane M. T. Lauzanne-Morelle, both of 170, Ave. Parmentier, 75010 Paris, France

[21] Appl. No.: 324,004

[22] Filed: Nov. 23, 1981

[30] Foreign Application Priority Data

Dec. 4, 1980 [FR] France ............................... 80 25732

[51] Int. Cl.³ .................. C07C 101/24; C07C 101/26
[52] U.S. Cl. .............................. 260/501.11; 424/319; 71/113
[58] Field of Search .................................. 260/501.11

[56] References Cited

FOREIGN PATENT DOCUMENTS

| | | | |
|---|---|---|---|
| 513125 | 5/1955 | Canada | 260/501.11 |
| 1435005 | 2/1965 | France | 260/501.11 |
| 773653 | 10/1955 | United Kingdom . | |
| 1034358 | 5/1963 | United Kingdom . | |
| 1067742 | 9/1963 | United Kingdom . | |
| 1080599 | 12/1963 | United Kingdom . | |
| 965637 | 8/1964 | United Kingdom | 260/501.11 |
| 1091089 | 10/1966 | United Kingdom . | |
| 1322482 | 1/1971 | United Kingdom . | |

*Primary Examiner*—Bernard Helfin
*Attorney, Agent, or Firm*—Eyre, Mann, Lucas & Just

[57] ABSTRACT

The compounds of formula

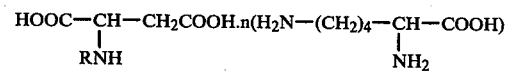

where R=H and n=1 or R=($C_6$-$C_{26}$)-acyl and n=2 are useful in the treatment of muscular fatigue and muscular contraction in men and animals and also in the stimulation of development in vegetation.

The compounds are claimed per se and in pharmaceutical and horticultural compositions. Methods of treatment of men, animals and vegetation are also claimed.

2 Claims, No Drawings

DERIVATIVES OF LYSINE AND ASPARTIC ACID

BACKGROUND OF INVENTION

There has for a long time been a need for a means of counteracting the effects of muscular fatigue and of temporary and involuntary muscular contractions, particularly in connection with sporting activities, wherein such physiological phenomena result from prolonged efforts.

OBJECT OF THE INVENTION

It is an object of the invention to satisfy the aforesaid need.

SUMMARY OF THE INVENTION

We have found that certain derivatives of lysine and aspartic acid have biological properties which counteract the effects of muscular fatigue and of temporary and involuntary muscular contractions. These derivatives, which form our invention, have the formula

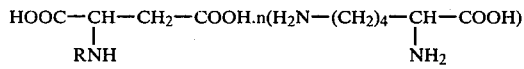

in which R represents a hydrogen atom and n is 1 or R represents a acyl group having from 6 to 26 carbon atoms and n is 2.

Lysine aspartate (R=H, n=1) may be prepared by the simple reaction of lysine with aspartic acid in an aqueous solution to a pH value of approximately 7. The lysine acyl aspartates (R=acyl, n=2) may be prepared by the total salination of the active amine function of lysine by a lipoamino acid, namely aspartic acid the amine function of which has been acylated by a compound containing an acyl group having from 6 to 26 carbon atoms.

In the lysine acyl aspartates, the acyl group may be saturated or unsaturated and may have a straight or branched chain. The acyl group is preferably selected from the group consisting of caproyl, capryl, lauryl, palmityl, undecenyl, oleyl and linoleyl groups.

The compounds of the invention are useful as the active ingredient of pharmaceutical compositions for topical application to men and animals and in methods of treating muscular fatigue and muscular contraction in men and animals by topical application. The compositions preferably contain from 0.5 to 10% by weight of the active ingredient.

We have further and surprisingly found that the compounds of the invention are of horitcultural use in stimulating the development of vegetation, particularly in the germination of seeds and in the treatment of leaves, the latter evidenced by a change in the intensity of the green colouration of the leaves upon such treatment. Our invention therefore emcompasses the new compounds, pharmaceutical and horticultural compositions containing them, and methods of treating men and animals against muscular fatigue and muscular contraction and of treating vegetation to stimulate its development.

DETAILED DESCRIPTION OF THE INVENTION

TABLE 1

| Type of Derivative | Molecular weight | Acid index | Theoretical Nitrogen | Actual Nitrogen |
|---|---|---|---|---|
| Lysine aspartate | 279 | 0 | 15% | 14.7% |
| Lysine capryl aspartate | 551 | 0 | 12.7% | 12.4% |
| Lysine Palmitic aspartate | 663 | 0 | 10.5% | 10.1% |
| Lysine Lauric aspartate | 607 | 0 | 11.5% | 11.3% |

Table 2 shows the results obtained in the treatment of muscular fatigue and the muscular decontraction effects obtained using lysine aspartate. Comparison is made with other aspartates.

TABLE 2

| Physiological Reaction | Lysine aspartate | Arginine aspartate | Ornithine aspartate | Guanidine aspartate |
|---|---|---|---|---|
| Relaxing effect | very marked | slight | slight | none |
| Muscular decontraction effect, involuntary or after effort | very marked | none | none | none |
| | very rapid | | | |

As can be seen, the effectiveness is due to the association of the aspartic acid with the lysine. The aspartates of the two other basic amino acids, arginine and ornithine, and of quanidine have little or no effect. Table 3 shows the results obtained with various lysine acyl aspartates.

TABLE 3

| Effects obtained | Nature of the acyl chain | | | | |
|---|---|---|---|---|---|
| | Acetyl | Butyl | Capryl | Lauryl | Palmityl |
| Relaxation of lower limbs | None | none | very marked | very marked | very marked |
| Effect on muscular decontraction | None | none | rapid | rapid | rapid |

It can be seen that lysine lower acyl aspartates are ineffective, whereas the lysine higher acyl aspartates according to the invention are notably effective.

The following formulations are examples of suitable pharmaceutical compositions according to the invention.

| 1. | Stearic acid | 5 |
| | Cetyl polyoxyethylene alcohol | 10 |
| | Isopropyl palmitate | 10 |
| | Glycerol | 10 |
| | Lysine aspartate | 1 to 10 |
| | Water to make up to 100 | |
| 2. | Glycerol stearate | 5 |
| | Beeswax | 10 |
| | Vaseline oil | 10 |
| | Sorbitol polyoxyethylene oleate | 5 |
| | Glycerol | 10 |
| | Lysine capryl aspartate | 1 to 10 |
| | Water to make up to 100 | |
| 3. | Stearic acid | 5 |
| | Cetyl polyethylene alcohol | 10 |

| -continued | |
|---|---|
| Ethyl stearate | 10 |
| Glycerol | 10 |
| Lysine palmityl aspartate | 1 to 10 |
| Water to make up to 100 | |

The following formulations are examples of suitable horticultural compositions according to the invention.

| (a) for the treatment of leaves | | |
|---|---|---|
| 1 | Lysine aspartate | 1 to 5 |
| | Water to make up to 100 | |
| 2. | Lysine capryl aspartate | 1 to 5 |
| | Water to make up to 100 | |
| 3. | Lysine lauryl aspartate | 1 to 5 |
| | Water to make up to 100 | |
| 4. | Unidecenyl aspartate | 1 to 5 |
| | Water to make up to 100 | |
| (b) for the treatment of seeds | | |
| 1. | Lysine aspartate | 0.5 to 10 |
| | Bentonite (Fullers earth) | |
| | to make up to 100 | |
| 2. | Lysine capryl aspartate | 0.5 to 10 |
| | Sodium lauryl collagenate | 5 |
| | Water to make up to 100 | |
| 3. | Lysine capryl aspartate | 0.5 to 10 |
| | Bentonite (Fullers earth) | |
| | to make up to 100 | |

We claim:

1. A derivative of lysine and aspartic acid having the general formula

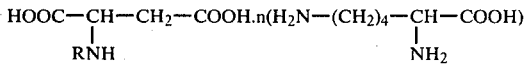

in which R represents an acyl group having from 6 to 26 carbon atoms and n is 2 and in which the acyl group is derived from an aliphatic moncarboxylic acid.

2. A derivative of lysine and aspartic acid having the general formula

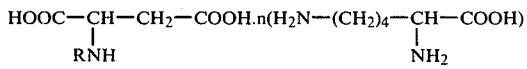

in which R represents an acyl group having from 6 to 26 carbon atoms and n is 2 and wherein the acyl group is selected from the group consisting of caproyl, capryl, lauryl, palmityl, undecenyl, oleyl and linoleyl groups.

* * * * *

UNITED STATES PATENT AND TRADEMARK OFFICE
CERTIFICATE OF CORRECTION

PATENT NO. : 4,447,366
DATED : May 8, 1984
INVENTOR(S) : Jean V. Morelle et al.

It is certified that error appears in the above-identified patent and that said Letters Patent are hereby corrected as shown below:

Column 1, line 58, delete "horitcultural" and substitute therefor --horticultural--.

Column 4, line 15, change "moncarboxylic" to --monocarboxylic--.

Signed and Sealed this

Second Day of October 1984

[SEAL]

Attest:

GERALD J. MOSSINGHOFF

Attesting Officer　　Commissioner of Patents and Trademarks